(12) United States Patent
Uehara et al.

(10) Patent No.: US 6,611,333 B1
(45) Date of Patent: Aug. 26, 2003

(54) ISOPOTOMER ABSORPTION SPECTRAL ANALYZER AND ITS METHOD

(75) Inventors: Kiyoji Uehara, Tokyo (JP); Naohiro Yoshida, Sagamihara (JP); Tomoyuki Kikugawa, Tokyo (JP)

(73) Assignees: Japan Science and Technology Corporation (JP); Anritsu Corporation (JP)

( * ) Notice: Subject to any disclaimer, the term of this patent is extended or adjusted under 35 U.S.C. 154(b) by 0 days.

(21) Appl. No.: 09/936,946

(22) PCT Filed: Mar. 22, 2000

(86) PCT No.: PCT/JP00/01743

§ 371 (c)(1),
(2), (4) Date: Sep. 20, 2001

(87) PCT Pub. No.: WO00/58712

PCT Pub. Date: Oct. 5, 2000

(30) Foreign Application Priority Data

Mar. 26, 1999 (JP) .............................. 11-084898

(51) Int. Cl.[7] .............................................. G01N 21/35
(52) U.S. Cl. ..................................... 356/432; 356/435
(58) Field of Search ............................... 356/432–436

(56) References Cited

PUBLICATIONS

Chemosphere Chem Biol Toxicol Relat Environ Probl, vol. 26, Nos. 1–4, pp. 13–22, 1993.

*Primary Examiner*—Frank G. Font
*Assistant Examiner*—Amanda Merlino
(74) *Attorney, Agent, or Firm*—Lorusso, Loud & Kelly

(57) ABSTRACT

An isotopomer absorption spectral analyzing apparatus and its method for precisely measuring the isotope ratio by substantially equalizing the absorption signal levels of different species of isotopes. In an isotopomer absorption spectral analyzing apparatus, a sample cell (21) capable of providing optical paths of different optical lengths is installed, optical beams A, B are caused to enter the sample cell (21) and travel along paths of different optical lengths, thereby determining the abundance ratio between species of isotopes in molecules from the ratio between intensities of signals corresponding to the species of isotopes.

4 Claims, 3 Drawing Sheets

ISOPOTOMER ABSORPTION SPECTRAL ANALYZER AND ITS METHOD

TECHNICAL FIELD

The present invention relates to an isotopomer absorption spectral analyzing apparatus and method for precisely assaying an isotopomer—a molecule containing an isotope—for inferring the origin thereof, contemplating applications in scientific fields, including environmental analysis; applications in the medical field, including diagnosis; and applications in other fields.

BACKGROUND ART

Conventional absorption spectral analyzing apparatuses employ a sample cell having a single optical path.

DISCLOSURE OF THE INVENTION

Therefore, when the isotope abundance ratio (the abundance ratio between two isotopes) deviates greatly from 1:1, a great difference is present between the levels of absorption signals corresponding to the isotope species, depending on the species of the isotopes. For example, in the case of naturally occurring $CH_4$, the abundance ratio of $^{12}CH_4$ to $^{13}CH_4$ is approximately 100:1, and therefore, the absorption signal level of $^{12}CH_4$ is approximately 100 times that of $^{13}CH_4$, making precise measurement of the isotope ratio difficult.

The present invention has been accomplished so as to solve the aforementioned problem. Thus, an object of the present invention is to provide an isotopomer absorption spectral analyzing apparatus and method which enable absorption signals corresponding to different isotopes to assume substantially the same level, to thereby enable precise measurement of the isotope ratio.

In order to achieve the above objects, the present invention provides the following.

[1] An isotopomer absorption spectral analyzing apparatus, characterized in that a sample cell having a single window for introduction of at least two optical beams into the cell and being capable of providing optical paths of different optical lengths is installed; at least two optical beams are caused to enter the sample cell such that the optical beams travel along optical paths of different optical path lengths; and the abundance ratio between species of isotopes in molecules is determined from the ratio between intensities of absorption signals corresponding to the species of isotopes.

[2] An isotopomer absorption spectral analyzing apparatus as described in [1], wherein the at least two optical beams are emitted from a single light source of variable-wavelength type or from a plurality of light sources of fixed-wavelength type or variable-wavelength type.

[3] An isotopomer absorption spectral analyzing apparatus as described in [1], wherein the sample cell is a multiple-reflection absorption cell having paired reflection mirrors.

[4] A method of isotopomer absorption spectral analysis, characterized in that a sample cell having a single window for introduction of at least two optical beams into the cell and being capable of providing optical paths of different optical lengths is used in order to substantially equalize levels of absorption signals corresponding to species of isotopes, to thereby enable precise measurement of the abundance ratio between the species of isotopes.

BEST MODES FOR CARRYING OUT THE INVENTION

A mode for carrying out the present invention will next be described in detail with reference to the drawings.

Figure 1:
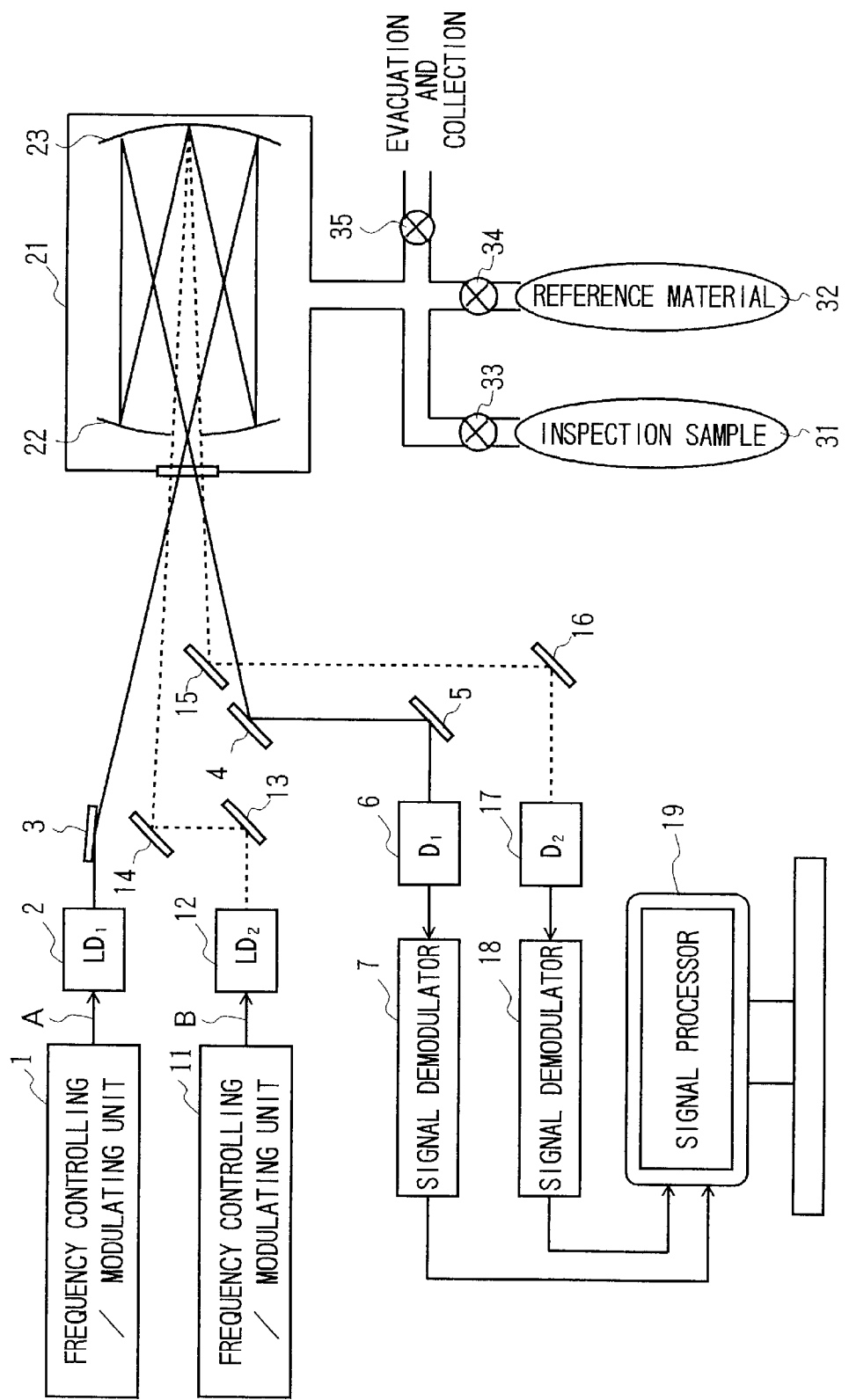
FIG. 1 shows the configuration of an isotopomer absorption spectral analysis system according to one embodiment of the present invention.

FIG. 1 is shows the configuration of an isotopomer absorption spectral analysis system according to one embodiment of the present invention. The system is based on laser spectroscopy employing a plurality of optical paths.

In FIG. 1, reference numeral 1 represents a first frequency controlling/modulating unit; reference numeral 2 represents a first laser diode $LD_1$; reference numerals 3, 4, and 5 represent reflection mirrors; reference numeral 6 represents a first optical detector $D_1$; reference numeral 7 represents a first signal demodulator; reference numeral 11 represents a second frequency controlling/modulating unit; reference numeral 12 represents a second laser diode $LD_2$; reference numerals 13, 14, 15, and 16 represent reflection mirrors; reference numeral 17 represents a second optical detector $D_2$; reference numeral 18 represents a second signal demodulator; reference number 19 represents a signal processor; reference numeral 21 represents a long-optical-path cell (sample cell: multiple-reflection absorption cell); reference numerals 22 and 23 represent paired reflection mirrors; reference number 31 represents an inspection sample (in which the abundance ratio of $^{12}CH_4$ to $^{13}CH_4$ is unknown); reference number 32 represents a reference material (in which the abundance ratio of $^{12}CH_4$ to $^{13}CH_4$ is known); and reference numerals 33, 34, and 35 represent open-close control valves. In the long-optical-path cell 21, a longer optical path is represented by a continuous line, and a shorter optical path is represented by a dotted line. The optical path length (determined by the number of times of reflection) is set through adjustment of the incident angle of the relevant optical beam and/or the angles of mirrors.

Optical beams A and B from the light sources are caused to enter, at different angles, the long-optical-path cell 21 serving as a multiple-reflection absorption cell and equipped with paired reflection mirrors 22 and 23, so that the optical beams A and B travel along optical paths of different lengths; e.g., 1 m and 100 m. Thus, an optical path difference suited for measuring the abundance ratio of a sample can be provided.

The abundance of an isotopomer (isotope-containing molecule) varies greatly in accordance with its origin and other factors. Accordingly, through precise measurement of the isotopomer abundance ratio of samples collected from many places in the world, formation, transfer, and disappearance of environmental substances can be analyzed in detail.

The present invention provides highly effective analysis means which supplements mass analysis conventionally employed for isotopomer analysis. In the method of the present invention, the ratio of the absorption signal of one isotopomer to that of another isotopomer is measured and compared with the same ratio of the reference material 32.

The $^{13}CH_4/^{12}CH_4$ ratio of methane contained in the atmosphere was measured. The ratio is known to be approximately 1/100. Thus, in order to obtain absolute absorption signals of substantially the same level, there may be employed either one of the following method (1) or (2): method (1) employing combination of a strong incident beam to be absorbed by $^{13}CH_4$ and a weak incident beam to be absorbed by $^{12}CH_4$, or method (2) employing two strong beams and causing them to travel along optical paths of different optical path lengths. In the present embodiment, the ratio was measured in accordance with the aforementioned method (2) by use of the method and analyzing apparatus of the present invention equipped with a modified Herriott long-optical-path cell (product of New Focus) and two wavelength-stabilized semiconductor lasers (laser diodes). The provided optical path lengths are 100 m and 1.1 m.

Figure 2:
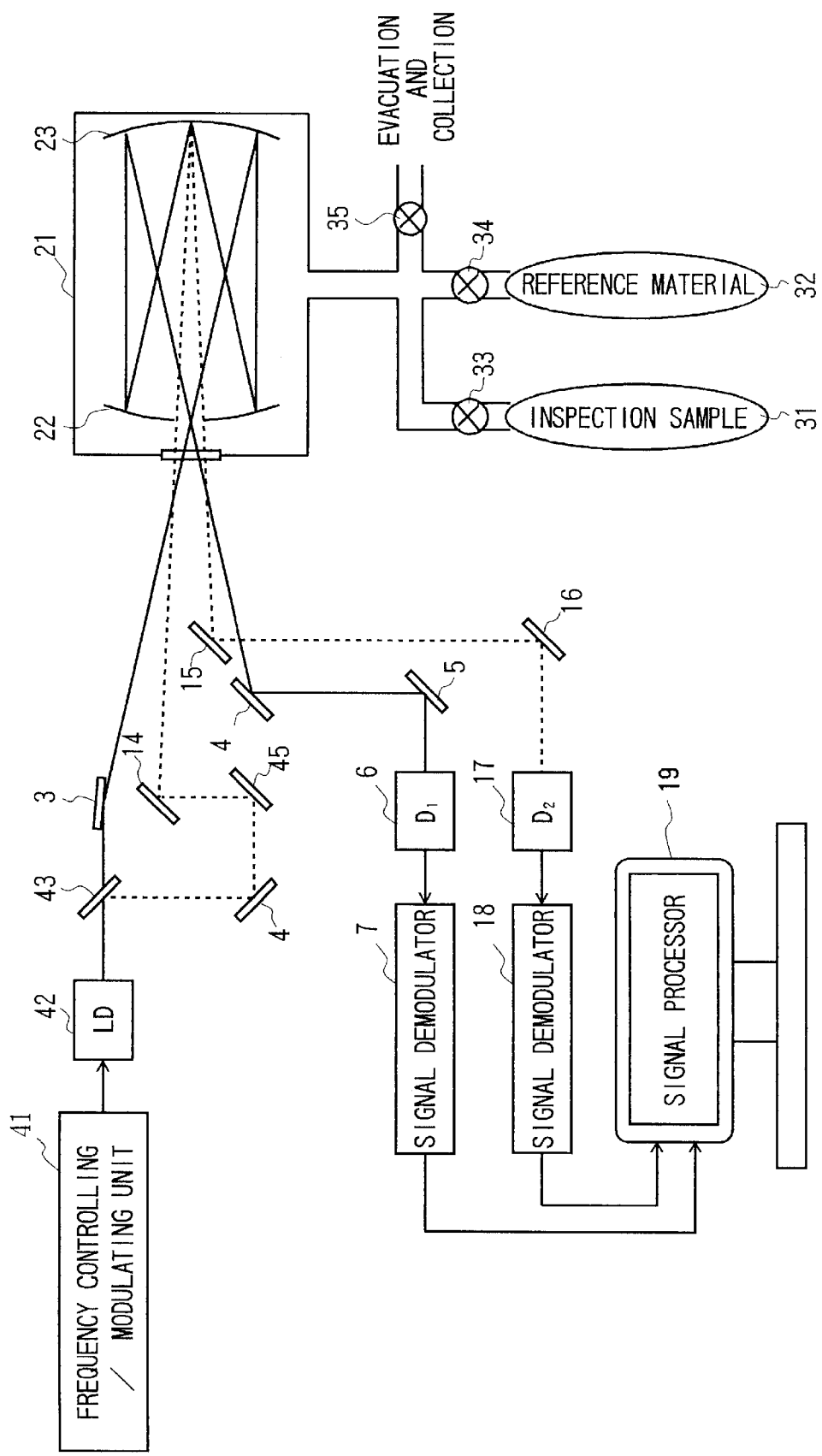
FIG. 2 shows a modification of the light source used in the isotopomer absorption spectral analysis system according to the embodiment of the present invention.

In the above embodiment, optical beams are generated by use of a plurality of light sources. Alternatively, as shown in FIG. 2, a plurality of optical beams may be generated by use of a single light source (laser diode LD) 42 and a semi-transparent mirror for dividing a beam from the light source. In FIG. 2, reference numeral 41 represents a frequency controlling/modulating unit, and reference numerals 44 and 45 represent reflection mirrors. Elements identical to those shown in FIG. 1 are represented by the same reference numerals as shown in FIG. 1, and repeated description thereof is omitted.

Figure 3:
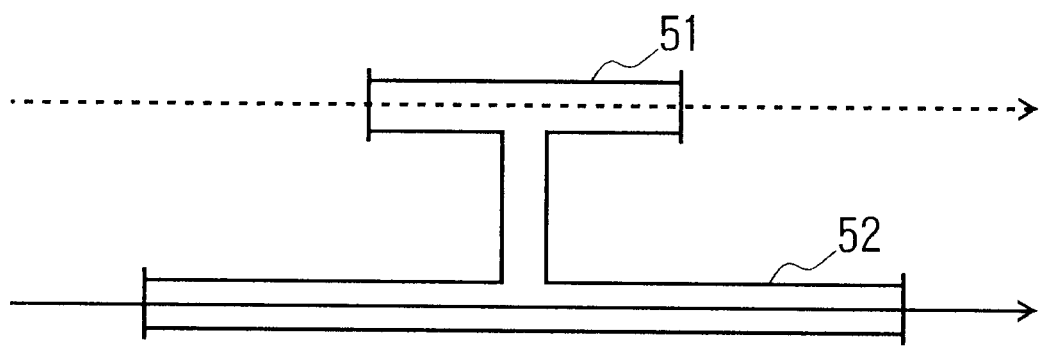
FIG. 3 shows a modification of the cell used in the isotopomer absorption spectral analysis system according to the embodiment of the present invention.

The aforementioned embodiment uses a cell including reflection mirrors, thereby providing a plurality of optical paths of different optical lengths. However, the structure of the cell is not limited to the aforementioned structure, and a cell as shown in FIG. 3; i.e., a cell having a short optical path portion 51 and a long optical path portion 52, may also be employed.

The present invention is not limited to the above-described embodiment. Numerous modifications and variations of the present invention are possible in light of the spirit of the present invention, and they are not excluded from the scope of the present invention.

As described in detail hereinabove, in the present invention, through employment of a sample cell capable of providing a plurality of optical paths of different optical lengths, the levels of absorption signals corresponding to isotope species can be substantially equalized in order to enable precise measurement of the isotope abundance ratio.

INDUSTRIAL APPLICABILITY

The present invention enables precise assay of an isotopomer—a molecule containing an isotope—for inferring the origin thereof. The invention is expected to find applications in scientific fields, including environmental analysis; and in medical fields including diagnosis.

What is claimed is:

1. An isotopomer absorption spectral analyzing apparatus comprising:

(a) a sample cell having a single window for introduction of at least two optical beams into the cell and being capable of providing optical paths of different optical lengths is installed; and (b) means for emitting at least two optical beams which enter the sample cell such that the optical beams travel along optical paths of different optical path lengths, whereby the abundance ratio between species of isotopes in molecules is determined from the ratio between intensities of absorption signals corresponding to the species of isotopes.

2. An isotopomer absorption spectral analyzing apparatus as described in claim 1, wherein the at least two optical beams are emitted from a single light source of variable-wavelength type or from a plurality of light sources of fixed-wavelength type or variable-wavelength type.

3. An isotopomer absorption spectral analyzing apparatus as described in claim 1, wherein the sample cell is a multiple-reflection absorption cell having paired reflection mirrors.

4. A method of isotopomer absorption spectral analysis, characterized in that a sample cell having a single window for introduction of at least two optical beams into the cell and being capable of providing optical paths of different optical lengths is used in order to substantially equalize levels of absorption signals corresponding to species of isotopes, to thereby enable precise measurement of the abundance ratio between the species of isotopes.

* * * * *

UNITED STATES PATENT AND TRADEMARK OFFICE
CERTIFICATE OF CORRECTION

PATENT NO. : 6,611,333 B1
DATED : August 26, 2003
INVENTOR(S) : Uehara et al.

It is certified that error appears in the above-identified patent and that said Letters Patent is hereby corrected as shown below:

<u>Title page,</u>
Item [56], References Cited, insert the following:
-- U.S. PATENT DOCUMENT
5,146,294    9/1992    Grisar et al    356/435

FOREIGN PATENT DOCUMENTS
10-197444   7/98    Japan
53-42890    4/78    Japan
9-297061    1/97    Japan --

Signed and Sealed this

Sixth Day of April, 2004

JON W. DUDAS
*Acting Director of the United States Patent and Trademark Office*